United States Patent [19]
> Arai et al.

[11] Patent Number: 5,004,685

[45] Date of Patent: Apr. 2, 1991

[54] DRY-TYPE MULTILAYER ANALYTICAL ELEMENT

[75] Inventors: Fuminori Arai; Asaji Kondo, both of Saitama, Japan

[73] Assignee: Fuji Photo Film Co., Ltd., Kanagawa, Japan

[21] Appl. No.: 86,514

[22] Filed: Aug. 18, 1987

[30] Foreign Application Priority Data

Aug. 19, 1986 [JP] Japan ................................ 61-193705

[51] Int. Cl.$^5$ .............................................. C12Q 1/26
[52] U.S. Cl. ........................................ 435/25; 435/10; 435/11; 435/14; 435/19; 435/28; 435/805; 436/904; 436/810; 422/56; 422/57
[58] Field of Search ....................... 435/10, 11, 14, 19, 435/25, 28, 805; 436/904, 810; 422/56, 57

[56] References Cited

U.S. PATENT DOCUMENTS

| | | | |
|---|---|---|---|
| Re. 29,498 | 12/1977 | Meiattini | 435/14 |
| Re. 30,267 | 5/1980 | Bruschi | 435/12 X |
| 3,411,887 | 11/1968 | Ku | 435/14 |
| 3,886,045 | 5/1975 | Meiattini | 435/14 X |
| 3,992,158 | 11/1976 | Przybylowicz et al. | 435/11 X |
| 4,042,335 | 8/1977 | Clément | 435/13 X |
| 4,283,491 | 8/1981 | Dappen | 435/10 |
| 4,291,121 | 9/1981 | Acquati et al. | 435/10 |
| 4,385,114 | 5/1983 | Güthlein et al. | 435/28 |
| 4,503,143 | 3/1985 | Gerber et al. | 435/28 X |
| 4,587,100 | 5/1986 | Amano et al. | 435/11 X |
| 4,732,736 | 3/1988 | Kobayashi et al. | 422/56 |
| 4,781,890 | 11/1988 | Arai et al. | 422/56 |
| 4,810,633 | 3/1989 | Bauer et al. | 435/25 |

FOREIGN PATENT DOCUMENTS

| | | | |
|---|---|---|---|
| 0239931 | 10/1987 | European Pat. Off. | 435/25 |
| 2546252 | 4/1976 | Fed. Rep. of Germany | 435/28 |
| 0218905 | 2/1985 | German Democratic Rep. | 435/28 |
| 57-63452 | 6/1982 | Japan | 422/56 |
| 7148250 | 12/1982 | Japan | 422/56 |
| 58-33450 | 2/1983 | Japan | 422/50 |

OTHER PUBLICATIONS

Patent Abstract of Japan, vol. 10, No. 314 (10/86), p. 39 C 380 and JP-A-61-124,393, Kobayashi et al.

Tietz, Ph.D., Norbert W., et al., *Textbook of Clinical Chemistry*, 1986; W. B. Saunders Company: Tokyo; pp. 882–888.

*Primary Examiner*—Esther L. Kepplinger
*Assistant Examiner*—Carol A. Spiegel
*Attorney, Agent, or Firm*—McAulay Fisher Nissen & Goldberg

[57] ABSTRACT

A dry-type multilayer analytical element containing a color reagent composition comprising an oxidase specifically reaction with an analyte or derived therefrom to produce hydrogen peroxide, hydrogen peroxide-decomposing enzyme, an alkali metal salt of ferrocyanide and a chromogen which is separated from the hydrogen peroxide-decomposing enzyme, the chromogen being incorporated in a layer nearer to the transparent support of the analytical element than the layer containing the hydrogen peroxide-decomposing enzyme. The analytical element exhibits excellent coloration, color stability, and accuracy and the results are minimally influenced by the presence of hemoglobin in the sample.

18 Claims, 1 Drawing Sheet

DRY-TYPE MULTILAYER ANALYTICAL ELEMENT

BACKGROUND OF THE INVENTION

1. Field of the Invention

This invention relates to a dry-type multilayer analytical element for analysis of an analyte (the object substance to be analyzed) in a liquid sample where the analyte directly or indirectly produces hydrogen peroxide in the presence of oxidase. More particularly, this invention relates to a dry-type multilayer analytical element for analysis of an analyte in a liquid sample containing oxidase, a hydrogen peroxide-decomposing enzyme ($H_2O_2$-decomposing enzyme), a ferrocyanide and a chromogen as essential components wherein the $H_2O_2$-decomposing enzyme is incorporated in a layer more distant from the support of the analytical element than the layer containing the chromogen.

2. Description of Prior Art

In clinical chemical analysis, a widely used colorimetric method determines the $H_2O_2$ produced from an analyte in a sample, such as, serum by using an oxidase of which the substrate is the analyte or an oxidase of which the substrate is a substance derived from the analyte. The $H_2O_2$ is usually allowed to oxidize a chromogen in the presence of a $H_2O_2$-decomposing enzyme such as peroxidase (POD). The chromogen can be divided into two groups, i.e. leuco dye type chromogens oxidized to form color materials from themselves and coupling type chromogens which are oxidized and then coupled with a coexisting coupler to form colored materials. The oxidized coupling type chromogen itself does not have a color.

Various reagent compositions have been developed for determination of analytes utilizing $H_2O_2$ produced from them, and various analytical elements for dry-type analysis are also known. As the examples of the reagent compositions containing ferrocyanide as an essential component for determination of $H_2O_2$, U.S. Pat. No. 3,886,045 (U.S. Re. No. 29,498) discloses a reagent composition for determination of glucose comprising glucose oxidase, POD, 4-aminoantipyrine (4-AA), a coupler, such as, phenol and ferrocyanide. U.S. Pat. No. 4,291,121 discloses a reagent composition for determination of uric acid or cholesterol comprising uricase (uric acid oxidase) or cholesterol oxidase, POD, 4-AA, a coupler, such as, 3,5-dichloro-2-hydroxybenzene sulfonic acid or its Na or K salt and ferrocyanide.

It is disclosed in these patent documents that ferrocyanide can eliminate the influence of a reductive substance particularly bilirubin in a sample which is an interfering material for the determination. However, the inventors have found that only a limited selection of chromogens must be used, because all the components are allowed to coexist irrespective of the usual chemical analysis or dry-type analytical element. Furthermore, the applicable analytes are restricted to the above three substances, and the color produced is unstable in the case of a dry-type analytical element.

Japanese Patent KOKOKU No. 37-5796 discloses another example of a reagent composition for the determination of glucose comprising glucose oxidase, POD, leuco dye and potassium ferrocyanide. All of these components are allowed to coexist. In this case, potassium ferrocyanide is added as a reductant for decoloration of the dye formed by oxidation of $H_2O_2$-POD.

As described above, when an analyte was determined by using a reagent composition comprising an oxidase specifically reacting with the analyte to produce $H_2O_2$, POD, chromogen and ferrocyanide, these all components were added to one solution or one layer. As a result, coloration and decoloration proceeds in parallel, and thereby the accuracy of the results are lowered. Particularly, in the case that the evolution of $H_2O_2$ is abundant or in the case that the chromogen employed is 3-substituted imidazole leuco dye, this phenomenon is pronounced. This matter suggest that coexisting $H_2O_2$ is a cause of the decoloration of the color material produced.

The reaction formula in the case of cholesterol is shown below.

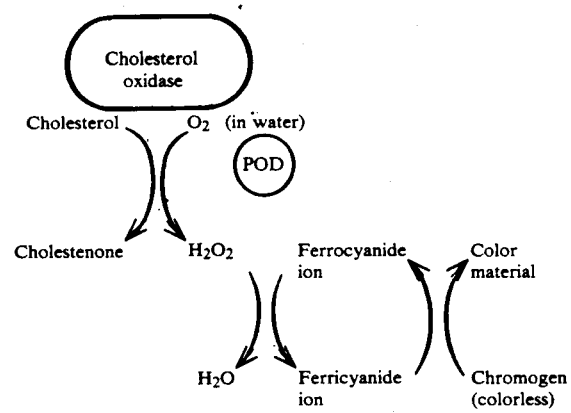

This reaction formula is suggested in Japanese Patent KOKAI No. 49-50991 and by Fossati et al. ("Clinical Chemistry", 26 (2), 227–231 (1980)). Besides, a dry-type analytical element containing these four components is disclosed in Japanese Patent KOKAI No. 56-15582. This analytical element is formed of a test paper (reagent strip) impregnated with a solution containing a reagent composition for determination of cholesterol or uric acid comprising the above four components and then dried.

A dry-type multilayer analytical element is superior to such a test paper in operation and quantitation (Asaji Kondo "Bunseki (Analysis)" 1984 (7), 534). The present inventors have prepared a multilayer analytical element for determination of cholesterol containing the above four components in one layer according to the method of D. M. Dappen et al. ("Clinical Chemistry", 28 (5), 1159 (1982)). And, they have found that in the case of this analytical element, the colored material formed was unstable, and it was decolored during measuring.

While, Japanese Patent KOKAI No. 61-124393 discloses a multilayer analytical element for detecting hydrogen peroxide containing peroxidase, a hydrogen donor corresponding to the coupling type chromogen in the analytical element of the invention and a coupler. In this patent, the separation of peroxidase from the hydrogen donor is proposed for the purpose to improve the stability in storage of the analytical element by preventing the deterioration of peroxidase. However, this patent does not refer to the incorporation of a ferrocyanide which also brings deterioration of the analytical element by reacting with other components of the reagent composition and a polymer binder.

SUMMARY OF THE INVENTION

Accordingly, an object of the invention is to provide a dry-type multilayer analytical element for determination of an analyte in a liquid sample by determining the $H_2O_2$ produced in the presence of oxidase which has a high reliability and a wide use.

Another object of the invention is to provide a dry-type multilayer analytical element which eliminates the error caused by the interference of hemoglobin in a blood sample.

Still another object of the invention is to provide a dry-type multilayer analytical element containing a color forming reagent composition for determination of $H_2O_2$ capable of determining $H_2O_2$ in a high accuracy.

The present inventors have investigated in order to achieve such objects, and they have found that when the chromogen is incorporated in a layer which is separate from the oxidase, POD and ferrocyanide, decoloration does not occur, and many advantages are obtained.

Thus, the present invention provides a dry-type multilayer analytical element having a layer containing a color forming reagent composition capable of determining the amount of an analyte in an aqueous liquid sample by measuring the hydrogen peroxide produced in the presence of oxidase on a light-transmissive water-impermeable support, said color forming reagent composition comprises an oxidase specifically reacting with said analyte or a material derived from said analyte to produce hydrogen peroxide, a hydrogen peroxide-decomposing enzyme, a ferrocyanide and a chromogen as essential components, the layer containing said chromogen being separated from the layer containing said hydrogen peroxide-decomposing enzyme, and said layer containing the chromogen being disposed nearer to the support than said layer containing the hydrogen peroxide decomposing enzyme to said support.

DETAILED DESCRIPTION OF THE INVENTION

Figure 1:
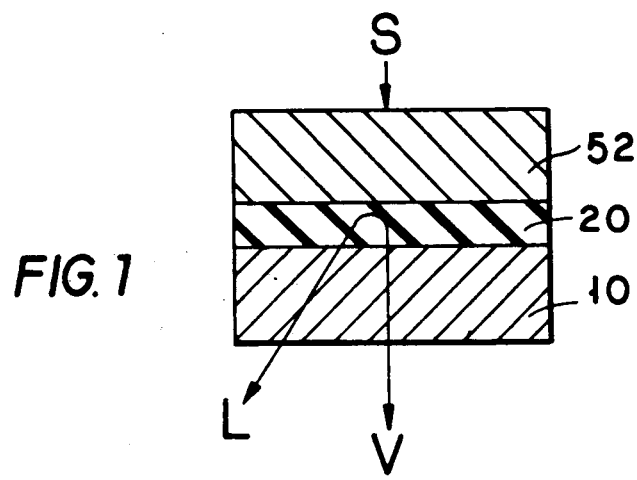
FIGS. 1 to 3 are schematic cross sectional views of the dry-type multilayer analytical element embodying the invention.
Figure 2:
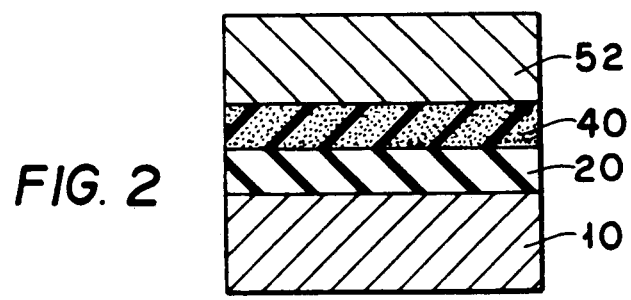
Figure 3:
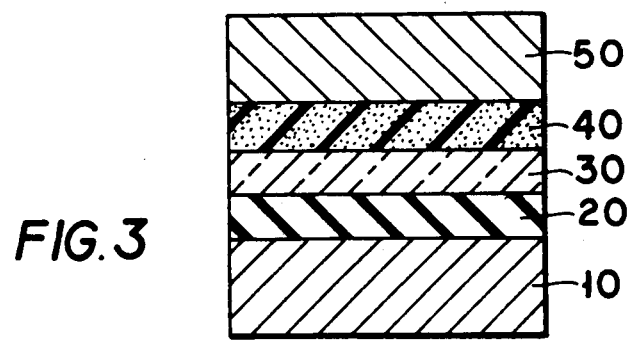

Some typical embodiments of the analytical elements of the invention are illustrated in FIGS. 1 to 3.

The analytical element of FIG. 1 is a fundamental structure, and composed of a light-transmissive water impermeable support 10, a chromogen containing layer 20 superposed on the support, and a porous spreading layer 52 containing reagents, such as, POD and an alkali salt of ferrocyanide (reagent-containing spreading layer). A liquid sample S is spotted on the spreading layer 52, and color developed in the chromogen containing layer 20 is measured from the side of the support 10 by reflection photometry. L indicates a light source, and V indicates the reflected light for measurements. For example, in the case of the analytical element for determination of cholesterol in a serum sample, a leuco type chromogen is utilized, and the reagent-containing spreading layer 52 having a structure disclosed in U.S. Pat. No. 3,992,158, U.S. Pat. No. 4,292,272 and Japanese Patent KOKAI No. 57-94658 contains POD, ferrocyanide, a reagent capable of reacting with cholesterol to produce $H_2O_2$, its auxiliary agents, a light-reflective material such as $BaSO_4$ particles or $TiO_2$ particles and the like. This reagent-containing spreading layer acts as a reagent layer, a light-reflecting layer and a sample spreading layer.

Another embodiment of the analytical element of the invention is illustrated in FIG. 2. This analytical element is composed of a light transmissive water-impermeable support 10, a chromogen-containing layer superposed on the support, a light-reflecting layer 40 containing titanium dioxide particles superposed on the chromogen-containing layer and a reagent-containing spreading layer 52 made of a woven fabric containing a $H_2O_2$ generating reagent composition composed of POD, ferrocyanide and cholesterol oxidase and auxiliary agent. The chromogen-containing layer 20 is apart more than several um from the reagent spreading layer 52 by the interposition of the light-reflecting layer 40.

Still another embodiment of the analytical element of the invention is illustrated in FIG. 3. This analytical element is a multilayer analytical element for determination of glucose which determines glucose concentration in the plasma component of a whole blood sample, and composed of a light-transmissive water-impermeable support 10, a chromogen containing layer 20 containing a coupling type chromogen (4-AA and a naphthol derivative) superposed on it, a hydrogen peroxide decomposing enzyme-containing layer 30 containing POD, ferrocyanide, glucose oxidase and auxiliary agent superposed thereon, a light-reflecting layer 40 also functioning as a color-blocking layer containing titanium dioxide particles superposed thereon, and a woven fabric spreading layer 50 spreading the whole blood sample spotted on it superposed thereon.

As shown in these drawings, chromogen is separated from other essential components of a reagent composition for determination of an analyte, and the chromogen-containing layer is interposed between the support and the hydrogen peroxide-decomposing enzyme-containing layer containing oxidase, POD and ferrocyanide. These analytical elements are preferably integral multilayer analytical element where respective layers are integrally laminated on the support.

The principle of the determination is explained as to the case of the embodiment of FIG. 2. A serum sample containing cholesterol is spotted on the reagent-containing spreading layer 52, and it spreads quickly into the reagent-containing spreading layer proportional to the spotted volume. The cholesterol in the serum is oxidized in the presence of cholesterol oxidase incorporated in the reagent containing spreading layer to generate $H_2O_2$. The $H_2O_2$ oxidizes ferrocyanide ion coexisting in this layer to ferricyanide ion. This ferricyanide ion passes through the light-reflecting layer 40, and reaches the chromogen-containing layer 20. In this layer, the ferricyanide ion oxidizes the chromogen to form a colored material. The production amount of the colored material is correlated with the amount of cholesterol in the serum.

Such an analytical element of the invention has various advantages.

First, since the oxidase oxidizing an analyte is incorporated in the outer layer or its vicinity, oxygen necessary to the reaction is readily supplied. Accordingly, oxidation reaction smoothly and quickly proceeds.

Second, the chromogen is incorporated in a layer apart from the $H_2O_2$ production place by analyte-oxidase reaction, and the chromogen is oxidized through intermediate processes such as $H_2O_2$—ferrocyanide ion—ferricyanide ion to form a colored material. Accordingly, the colored material hardly comes into contact with $H_2O_2$, and decoloration hardly occurs. This is particularly effective when the analyte content in a sample is abnormally high, resulting in a high production of $H_2O_2$.

Third, since the unstable chromogen incorporated in an inner layer comes into minimal contact with air, the stability of the analytical element is improved through its production, storage and use.

Fourth, in the case of conventional analytical elements containing the reagent composition composed of oxidase, POD, a ferrocyanide and chromogen, the chromogen is limited to coupling type (developer type), and the analyte is also limited to glucose, cholesterol and uric acid. However, in the case of the analytical element of the invention, leuco dye type chromogens can also be used, and any analyte capable of being a substrate of an oxidase can be analyzed.

Last, since the oxidase is incorporated in the outer layer or its vicinity, a lipophilic analyte, such as, cholesterol can readily be oxidized though it is hard to migrate in a hydrophilic binder layer. As a result, the variety of analytes capable of being analyzed by the analytical element of the invention is increased.

As the water-impermeable light-transmissive support, a known support employed in an usual multilayer analytical element may be employed. Such a support is a sheet or a film having a thickness in the range of from about 50 $\mu$m to about 1 mm, preferably from about 80 $\mu$m to about 0.3 mm and being transparent, i.e., capable of transmitting at least a part of the light having the wave length in the range from near-ultraviolet to near infrared regions. Such a sheet or a film may be made of a polyester (for example, polyethylene terephthalate or polycarbonate of bisphenol A), a cellulose ester (for example, cellulose diacetate, cellulose triacetate or cellulose acetate propionate), or polystyrene. A known undercoating layer or a known adhesive layer may be provided on the surface of the support in order to secure the adhesion of the support to its upper layer, such as, a water absorption layer or the chromogen-containing layer.

In the analytical element of the invention, a water absorption layer may be provided on the support. The water absorption layer is formed of a hydrophilic polymer which is swellable by water absorption as a principal component, and this layer absorbs the water to reach the surface of this layer. In the case of a whole blood sample, it accelerates permeation of the plasma component into the chromogen-containing layer. The swelling ratio of the hydrophilic polymer is in the range from about 150% to about 2000%, preferably about 250% to about 1500% at a water absorption at 30° C. Examples of the hydrophilic polymer are gelatin including acid treated gelatin and deionized gelatin, gelatin derivatives, such as, phthalated gelatin and hydroxyalkyl acrylate grafted gelatin, agarose, pullulan, pullulan derivatives, polyacrylamide, polyvinyl alcohol and polyvinyl pyrrolidone. They are disclosed in EP 0,119,861 A and EP 0,142,849 A. Preferable hydrophilic polymers are usually gelatin and gelatin derivatives. Polyacrylamide and polyvinyl alcohol are also preferable. The thickness of the water absorption layer is usually about 1 $\mu$m to about 100 $\mu$m in the dry state, and the range of about 3 $\mu$m to about 30 $\mu$m is preferable. The coating amount of this layer is about 1 g/m² to about 100 g/m², preferably about 3 g/m² to about 30 g/m². The water absorption layer may contain a known pH buffer, an organic carboxylic acid, an acid polymer or a base polymer in order to adjust the pH of this layer at the time of the analytical operation. The water absorption layer may also contain a known mordant, polymer mordant or the like. It is preferable that this layer is substantially transparent.

The chromogen-containing layer is a water-absorptive and water-permeable layer where a chromogen is uniformly incorporated in a hydrophilic polymer binder or a porous layer where a chromogen is uniformly incorporated. The hydrophilic polymer binder may be selected from the hydrophilic polymers described above. The thickness of the chromogen-containing layer is usually about 3 $\mu$m to about 50 $\mu$m in the dry state, and the range of about 5 $\mu$m to about 30 $\mu$m is preferable. The coating amount of this layer is about 3 g/m² to about 50 g/m², preferably about 5 g/m² to about 30 g/m². The chromogen-containing layer may contain a known pH buffer, an organic carboxylic acid, an acid polymer or a base polymer in order to adjust the pH of this layer at the time of the analytical operation. The chromogen-containing layer may also contain a known mordant, polymer mordant or the like. It is preferable that this layer is substantially clear, however this layer may contain a small amount of titanium dioxide particles, barium sulfate particles, carbon black or the like in order to control its optical property. The chromogen-containing layer may be a porous layer containing a chromogen (together with a coupler in the case of a coupling type chromogen) formed by the method described in EP 0 166 365A.

The hydrogen peroxide-decomposing enzyme-containing layer contains a hydrogen peroxide-decomposing enzyme, and it also contains oxidase and ferrocyanide for the introduction of an analyte into the coloring reaction system. In this layer, the analyte or a material derived from the analyte is oxidized by oxygen in the atmosphere in the presence of oxidase to produce hydrogen peroxide, and the hydrogen peroxide oxidizes ferrocyanide ion in the presence of hydrogen peroxide decomposing enzyme, such as, POD to ferricyanide ion. The ferricyanide ion produced diffuses into the chromogen-containing layer, and it oxidizes the chromogen to form a colored material. The hydrogen peroxide-decomposing enzyme-containing layer may contain a component for producing a substrate of the hydrogen peroxide-decomposing enzyme from an analyte, for example cholesterol esterase or an enzyme composition having cholesterol esterase activity for cholesterol ester.

The hydrogen peroxide-decomposing enzyme-containing layer is a porous layer containing hydrogen peroxide-decomposing enzyme, oxidase and ferrocyanide uniformly or a water absorptive water-permeable layer containing the above components in a hydrophilic polymer binder uniformly. In the case of the porous layer, this layer is preferably a porous spreading layer (reagent-containing spreading layer). The thickness of the reagent-containing spreading layer may be the same as the porous spreading layer not containing the above components. In the case of the hydrophilic polymer binder layer, this layer may be a nonporous layer or a porous layer containing particles as described in EP 0 114 403A. The thickness or coating amount of the hydrophilic polymer binder may be the same as the chromogen-containing layer described previously.

The porous spreading layer includes spreading layers of woven fabric disclosed in U.S. Pat. No. 4,292,272 and GB 2,087,074A, such as, plain weaves including broad cloth and poplin, spreading layers of knitted fabric disclosed in EP 0,162,302A such as, tricot fabric, double tricot fabric and milanese fabric, spreading layers composed of a paper containing fibrous pulp of an organic polymer disclosed in Japanese Patent KOKAI No. 57-148250, membrane filters (blushed polymer layer) disclosed in U.S. Pat. No. 3,992,158, continuous microspaces-containing porous layers where polymer particulates, glass particulates or diatomaceous earth are dispersed in a hydrophilic polymer binder, continuous microspaces-containing porous layers where polymer particulates, glass particulates, etc. are joined so as to contact each other at a point by using a polymer adhesive which does not swell in water (three-dimensional lattice structure layer) disclosed in U.S. Pat. No. 4,258,001. When the color reagent composition is incorporated in the spreading layer, the preferable spreading layers are fibrous spreading layers, such as, the spreading layers of woven fabric and the spreading layers of knitted fabric.

In order to increase the adhesive force, the above fibrous porous spreading layer, such as, woven fabrics, knitted fabrics and papers may be made hydrophilic by a physical activation treatment, such as, glow discharge or corona discharge disclosed in GB 2,087,074A, a chemical treatment, such as, washing, degreasing and immersing in a hydrophilic polymer solution, disclosed in U.S. Pat. No. 4,292,272 and GB 2,087,074A, or a combination thereof.

A color-blocking layer or a light-reflecting layer may be provided between the reagent layer or a water-absorption layer and the porous spreading layer. The color-blocking layer or the light-reflecting layer is composed of a hydrophilic polymer binder, such as, gelatin where white particles, such as, titanium dioxide particles or barium sulfate particles are uniformly suspended. The thickness of this layer is about 2 $\mu$m to about 20 $\mu$m in dry state.

An adhesive layer may be provided in order to fortify the adhesive force to the spreading layer. This layer is composed of the hydrophilic polymer mentioned previously, such as, gelatin, and its dry thickness is about 0.5 $\mu$m to about 5 $\mu$m.

A surfactant, such as, a nonionic surfactant may be incorporated in the reagent layer, water-absorption layer, color-blocking layer light-reflecting layer, adhesive layer or spreading layer. Examples of the nonionic surfactant are p-octylphenoxypolyethoxyethanol, p-nonylphenoxypolyethoxy-ethanol, polyoxyethylene oleyl ether, polyoxyethylene sorbitan monolaurate, p-nonylphenoxypolyglycidol (nonylphenyl polyglycidyl ether), octylglucoside and the like. The spreading action (metering action) of the spreading layer is improved by incorporating a nonionic surfactant in the spreading layer. When a nonionic surfactant is incorporated in the reagent layer or the water-absorption layer, these layers readily absorb the water in an aqueous sample uniformly. Moreover, the liquid in the spreading layer quickly and uniformly permeates into these layers. The content of a nonionic surfactant is usually about 20 mg to about 15 g, preferably about 50 mg to about 10 g for each layer capable of incorporating it.

The oxidase catalyzes the oxidation of the analyte or a material derived from the analyte. Such an oxidase is selected according to the kind of analyte, and includes oxidases of glucose, cholesterol, urate, lactate, glycerol, choline, polyamines, organic acids, alcohols, phenols or amino acids, and oxidases of the materials derived from glycerophosphate, sarcosine, pyruvate, choline, glycolate or acylcoenzyme A. These oxidases are described in "Koso (Enzyme) Handbook" (Ed. by Maruo, Tamiya et al., Asakura Shoten, Tokyo, 1982), "Rinsho Koso (Clinical Enzyme) Handbook" (Ed. by Baba, Wada, Kitamura and Okuda, Kodansha, Tokyo, 1982), "Enzymes 3rd. Ed." Ed. by M. Dixon and E. C. Webb, Longman, London, 1979) and "Methods of Enzymatic Analysis 3rd. Ed." (Ed. by H. U. Bergmeyer et al., Weinheim, Verlag Chimie, 1983-1986). Moreover, this oxidase also includes the oxidase bound to antigen, hapten or antibody as a labelling substance used in an immunoassay and the oxidase liberated by an immunological reaction. The content of the oxidase is usually about 100 U to about 100,000 U, preferably about 300 U to about 60,000 U per 1 $m^2$ of analytical element.

The hydrogen peroxide-decomposing enzyme includes peroxidase (POD), catalase and various enzymes having hydrogen peroxide decomposing activity contained in a biological fluid, such as, blood described in the foregoing books. POD is the most popular enzyme.

The peroxidase (EC 1.11.1.7) may be plant origin or animal origin described in the foregoing books, U.S. Pat. No. 3,983,005 or Japanese Patent KOKOKU No. 57-5520 or microbial origin described in Japanese Patent KOKOKU No 58-5035. Preferable peroxidases are nonspecific peroxidases of plant origin or micorbial origin, such as horseradish peroxidase, Japanese radish peroxidase, the peroxidase produced by a Cochliobolus genus microorganism and the peroxidase produced by a Curvularia genus microorganism. The content of peroxidase is preferably 2,000 U to about 60,000 U per 1 $m^2$ of analytical element. A known pH buffer may be incorporated in the layer containing peroxidase or an adjacent layer in order to maintain a pH 5.0 to 8.0, preferably pH 6.0 to 7.0 at the time of analytical operation.

The ferrocyanide is a compound containing or capable of liberating ferrocyanide ion $(Fe(CN)_6^{4-}$. Such a ferrocyanide includes various alkali metal salts, alkaline earth metal salts and mixtures of them. Examples of the ferrocyanide are sodium ferrocyanide, potassium ferrocyanide, lithium ferrocyanide, magnesium ferrocyanide and calcium ferrocyanide. Among them, sodium ferrocyanide and potassium ferrocyanide are preferable. The content of the ferrocyanide is about 0.1 m mol. to about 10 m mol., preferably about 0.5 m mol. to about 5 m mol. per $m^2$ of analytical element.

The chromogen may be either a leuco dye type (self-developing type) or coupling type (developer type). The leuco dye type chromogen includes benzidine type compounds, diphenylamine type compounds, triarylmethane type compounds, 3-substituted imidazole type compounds and the like. Examples of the leuco dye type chromogen are triarylimidazole leuco dyes, such as, 2-(4-hydroxy-3,5-dimethoxyphenyl)-4,5-bis[4-(dimethylamino)phenyl]imidazole described in U.S. Pat. No. 4,089,747, diarylimidazole leuco dyes, such as, 2-(3,5-dimethoxy-4-hydroxyphenyl)-4-[4-(dimethylamino)-phenyl]-5-phenethylimidazole described in EP 0 122 641A, diarylimidazole leuco dyes, such as, 2-(3,5-dimethoxy-4-hydroxyphenyl)-4-[4-(dimethylamino)phenyl]-5-methylimidazole and 2-(3,5-dimethoxy-4-hydroxyphenyl)-4-[4-(dimethylamino)phenyl]-5-(4-hydroxybutyl)imidazole described in U.S. Pat. No. 4,665,023, and diarylmonoheteroarylimidazole leuco dyes such as 2-(2-phenyl-3-indolyl)-4,5-di[4-(dimethylamino)phenyl]imidazole described in EP 0 122 641A. The coupling type chromogen includes antipyrine (phenazone) type compounds, benzothiazolinone hydrazone type compounds, and the like. Examples of the coupling type chromogen are 4-aminoantipyrine (4-aminophenazone, 1-phenyl-2,3-dimethyl-4-amino-3-pyrazolin-5-one) described in Ann. Clin. Biochem., 6, 24–27 (1969), and 4-aminoantipyrine analogs such as 1-di or tri-substituted phenyl-2,3-dimethyl-4-amino-3-pyrazolin-5-ones such as 1-(2,4,6-trichlorophenyl)-2,3-dichlorophenyl)-2,3-dimethyl-4-amino-3-pyrazolin-5-one described in EP 0 103 901A and 1-phenyl-2,3-dimethylamino-3-pyrazoline-5-one and the like described in Japanese Patent KOKAI No. 49-50991. Preferable coupling type chromogens are 4-aminoantipyrine, 1-(2,4,6-trichlorophenyl)-2,3-dimethyl-4-amino-3-pyrazolin-5-one and 1-(3,5-dichlorophenyl)-2,3-dimethyl-4-amino-3-pyrazolin-5-one. The coupler combined with coupling type chromogen includes phenol type compounds, naphthol type compounds, aniline type compounds and primaquine. Examples of the coupler are phenol, phenolsulfonic acids (including their alkali metal salts and alkaline earth metal salts), such as, 2-hydroxy-1-benzenesulfonic acid, 4-hydroxy-1-benzenesulfonic acid, 3,5-dichloro-2-hydroxy-1-benzenesulfonic acid and 2-hydroxy-3-methoxy-1-benzenesulfonic acid, 1-naphthol, 2-naphthol, dihydroxynaphthalenes, such as, 1,7-dihydroxynaphthalene, naphtholsulfonic acids (including their alkali metal salts and alkaline earth metal salts), such as, 1-hydroxy-2-naphthalenesulfonic acid and 1-hydroxy-4-naphthalenesulfonic acid and other phenol or naphthol derivatives. They are described in Ann. Chin. Biochem., 6, 24–27 (1969), U.S. Pat. Nos. 3,983,005, 4,042,335, 4,350,762 and Japanese Patent KOKAI Nos. 49-50991, 55-164356, and 56-155852. Preferable couplers are 1,7-dihydroxynaphthalene, 1-hydroxy-2-naphthalenesulfonic acid, 3,5-dichloro-2-hydroxy-1-benzenesulfonic acid and 2-hydroxy-3-methoxy-1-benzenesulfonic acid. The above benzenesulfonic acids include their Na salts, K salts and Li salts. The content of the chromogen is about 0.5 m mol. to about 10 m mol., preferably about 1 m mol. to about 5 m mol., irrespective of the leuco dye type (self-developing type) chromogen and the coupling type chromogen. The content of the coupler combining with the coupling type chromogen is about 0.5 m mol. to about 40 m mol. preferably about 1 m mol. to about 20 m mol.

A known pH buffer may be incorporated in the analytical element of the invention in order to adjust the reaction pH to the optimum pH at the time of the analytical operation. Suitable pH buffers are described in "Kagaku Benran (Chemical Handbook) Kiso Hen (Fundamental Volume)" pp 1312–1320, (Ed. by The Chemical Society of Japan, Maruzen, Tokyo, 1966), "Data for Biochemical Research 2nd Ed." pp 476–508 (Ed. by R. M. C. Dawson et al., Oxford at the Clarendon Press, 1969), "Biochemistry", 5, 467–477 (1966) and "Analytical Biochemistry" 104, 300–310 (1980). Example of the pH buffer are buffers containing tris (hydroxymethyl)aminomethane (Tris), buffers containing phosphate, buffers containing borate, buffers containing citric acid or citrate and buffers containing glycine. Preferable buffers are potassium dihydrogen phosphate disodium hydrogen phosphate, Tris-sodium borate, Tris-sodium borate-EDTA.2Na, Tris citric acid, acetic acid-sodium acetate and citric acid-sodium dihydrogen phosphate.

The analytical element of the invention can be prepared according to a known method described in the foregoing patent.

For use, the integral multilayer analytical element of the invention is preferably cut into square or circular pieces having a side or diameter of about 15 mm to about 30 mm, and put in a slide frame disclosed in U.S. Pat. No. 4,169,751, Japanese Patent KOKAI No. 57-63452, U.S. Pat. No. 4,387,990 and Japanese Utility Model KOKAI No. 58-32350, U.S. Pat. No. 4,169,751, U.S. Pat. No. 4,387,990, PCT application WO 83/00391, etc. While, the analytical element may be supplied in a form of a long tape packaged in a cassette or a magazine or in a form of small pieces stuck on or placed in a card having an opening.

The measurement is carried out, for example, according to the manner disclosed in the specifications of the foregoing patents. About 5 $\mu$l to about 30 $\mu$l, preferably about 8 $\mu$l to about 15 $\mu$l of an aqueous sample is spotted on the spreading layer, and incubated at a definite temperature in the range of about 20° C. to about 45° C. for 1 to 10 minutes. Thereafter, a detectable change, such as, color change or coloring in the multilayer analytical element is measured from the side of the support through reflection photometry, and the subject component in the sample is determined by the principle of colorimetry. When this measurement is carried out by using the chemical analytical apparatus disclosed in U.S. Pat. Nos. 4,488,810, 4,424,191 and 4,424,191, highly accurate results can easily be obtained by a simple operation.

EXAMPLES

EXAMPLE 1

The support employed was a colorless transparent polyethylene terephthalate (PET) film having a thickness of 180 $\mu$m on which a gelatin undercoating was provided. The aqueous solutions of the following layers were successively coated and dried to form a laminate.

| Chromogen-containing layer: | |
|---|---|
| Alkali-treated gelatin | 23 g/m² |
| Nonylphenylpolyglycidyl ether | 1.0 g/m² |
| (Containing 10 glycidyl units on average) | |
| 1,7-Dihydroxynaphthalene | 230 mg/m² |
| Aminoantipyrine | 960 mg/m² |
| Bis(vinylsulfonylmethyl)ether | 250 mg/m² |
| Light-blocking layer: | |
| Alkali-treated gelatin | 3.8 g/m² |
| Rutile type titanium dioxide particles | 40 g/m² |
| Nonylphenylpolyglycidyl ether | 1.3 g/m² |
| (Containing 10 glycidyl units on average) | |
| Adhesive layer: | |
| Alkali-treated gelatin | 6.7 g/m² |
| Nonylphenylpolyglycidyl ether | 260 mg/² |
| (Containing 10 glycidyl units on average) | |

The adhesive layer was uniformly dampened with 30 g/m² of water, and a PET tricot fabric cloth was lightly pressed to laminate thereon as the spreading layer. This tricot fabric cloth was made by knitting 50D PET spun yarn using 36 gauge, and its thickness was about 250 $\mu$m. Subsequently, the following aqueous color forming reagent composition solution for determination of cholesterol was applied on the spreading layer, and dried to obtain the integral multilayer analytical element for the determination of cholesterol.

Color forming reagent composition for the determination of cholesterol:

| | |
|---|---|
| Nonylphenoxypolyethoxyethanol | 160 mg/m² |

-continued

| | |
|---|---|
| (Containing 9-10 hydroxyethylene units on average) | |
| Monopotassium dihydrogen phosphate | 45 mg/m² |
| Dipotassium monohydrogen phosphate | 80 mg/m² |
| Cholesterol esterase | 4,500 U/m² |
| Cholesterol oxidase | 800 U/m² |
| Peroxidase | 4,000 U/m² |
| Potassium ferrocyanide | 130 mg/m² |
| Polyvinyl pyrrolidone (Mean molecular weight; 360,000) | 2.7 g/m² |

The multilayer analytical element for the determination of cholesterol thus obtained was cut into square pieces 15 mm on a side, and put in a slide frame described in Japanese Patent KOKAI No. 58-32350.

COMPARATIVE EXAMPLE 1

A comparative multilayer analytical element for the determination of cholesterol was prepared in the same manner as Example 1, except that potassium ferrocyanide and peroxidase were not added to the color forming reagent composition for determination of cholesterol and the following color forming reagent layer was provided instead of the chromogen-containing layer:

Color forming reagent layer:

| | |
|---|---|
| Alkali-treated gelatin | 23 g/m² |
| Nonylphenylpolyglycidyl ether (Containing 10 glycidyl units on average) | 1.0 g/m² |
| Peroxidase | 4,000 U/m² |
| 1,7-Dihydroxynaphthalene | 230 mg/m² |
| 4-Aminoantipyrine | 960 mg/m² |
| Bis(vinylsulfonylmethyl) ether | 250 mg/m² |

This comparative multilayer analytical element was also cut into square pieces and put in a slide frame in the same manner as Example 1.

COMPARATIVE EXAMPLE 2

Another comparative multilayer analytical element for the determination of cholesterol was prepared in the same manner as Example 1, except that peroxidase was not added to the color forming reagent composition for determination of cholesterol and the same color forming reagent layer as above was provided instead of the chromogen-containing layer. This comparative multilayer analytical element was also cut into square pieces and put in a slide frame in the same manner as Example 1.

EXAMPLE 2

The above three analytical elements were evaluated as follows.

In order to make each calibration curve, five human plasmas having different cholesterol concentrations were prepared, and respective cholesterol concentrations were determined by the method of C. C. Allain described in Clinical Chemistry, 20 (4), 470-475 (1974). Each 10 μl of these five human plasmas was spotted on the spreading layer of each analytical element mounted on the slide frame, and incubated at 37° C. for 6 minutes. Immediately, reflective optical density of the chromogen-containing layer or the color forming reagent layer was measured from the side of the support by reflection photometry using a visible light having a central wavelength at 640 nm.

The results are shown in Table 1.

TABLE 1

| Cholesterol Concentration | Reflective Optical Density | | |
|---|---|---|---|
| mg/dl | Example 1 | Comparative 1 | Comparative 2 |
| 52 | 0.440 | 0.450 | 0.208 |
| 104 | 0.662 | 0.669 | 0.212 |
| 180 | 0.945 | 0.890 | 0.167 |
| 315 | 1.207 | 1.003 | 0.299 |
| 380 | 1.313 | 0.929 | 0.331 |

Subsequently, three control sera were prepared from a serum containing 110 mg/dl of cholesterol and no hemoglobin by adding hemoglobin in hemoglobin concentrations of 0 mg/dl (not added), 250 mg/dl and 500 mg/dl. Each 10 μl of the control sera was spotted on the spreading layer of each analytical element mounted on the slide frame, incubated, and then reflective optical density was measured in the same manner as above. The results are shown in Table 2.

TABLE 2

| Hemoglobin Concentration | Reflective Optical Density (Error %) | |
|---|---|---|
| mg/dl | Example 1 | Comparative 1 |
| 0 | 0.684 (Criterion) | 0.679 (Criterion) |
| 250 | 0.688 (+0.6%) | 0.604 (−11.0%) |
| 500 | 0.677 (−1.0%) | 0.582 (−14.3%) |

As shown in the table, the error caused by the interference of hemoglobin is extremely small.

EXAMPLE 3

The support employed was a colorless transparent polyethylene terephthalate (PET) film having a thickness of 180 μm on which a gelatin undercoating was provided. The aqueous solutions of the following layers were successively coated and dried to form a laminate.

| | |
|---|---|
| Chromogen-containing layer: | |
| Alkali-treated gelatin | 23 g/m² |
| Nonylphenylpolyglycidyl ether (Containing 10 glycidyl units on average) | 1.0 g/m² |
| 1,7-Dihydroxynaphthalene | 230 mg/m² |
| 4-Aminoantipyrine | 960 mg/m² |
| Bis(vinylsulfonylmethyl)ether | 250 mg/m² |
| Light-blocking layer: | |
| Alkali-treated gelatin | 3.8 g/m² |
| Rutile type titanium dioxide particles | 40 g/m² |
| Nonylphenylpolyglycidyl ether (Containing 10 glycidyl units on average) | 1.3 g/m² |
| Adhesive layer containing peroxidase: | |
| Alkali-treated gelatin | 6.7 g/m² |
| Nonylphenylpolyglycidyl ether (Containing 10 glycidyl units on average) | 1.0 mg/m² |
| Potassium ferrocyanide | 0.5 g/m² |
| Peroxidase | 1,600 U/m² |
| Glucose oxidase | 600 U/m² |

The adhesive layer was uniformly dampened with 30 g/m² of water, and a 100% cotton plain weave fabric was lightly pressed to laminate thereon as the spreading layer, and dried to obtain the integral multilayer analytical element for determination of glucose. This plain weave fabric was formed by 100 two ply yarn, and its thickness was about 140 μm. This element was cut and put in the slide frame similarly to Example 1.

COMPARATIVE EXAMPLE 3

The support employed was a colorless transparent polyethylene terephthalate (PET) film having a thickness of 180 μm on which gelatin under coating was provided. The aqueous solutions of the following layers were successively coated and dried to form a laminate.

| Color forming reagent layer: | |
|---|---|
| Alkali-treated gelatin | 20 g/m² |
| Nonylphenylpolyglycidyl ether | 900 g/m² |
| (Containing 10 glycidyl units on average) | |
| 1,7-Dihydroxynaphthalene | 200 mg/m² |
| 4-Aminoantinyrine | 850 mg/m² |
| Glucose oxidase | 4,000 U/m² |
| Peroxidase | 7,000 U/m² |
| Bis(vinylsulfonylmethyl) ether | 220 mg/m² |
| Light-blocking layer: | |
| Alkali-treated gelatin | 3.8 g/m² |
| Rutile type titanium dioxide particles | 40 g/m² |
| Nonylphenylpolyglycidyl ether | 1.3 g/m² |
| (Containing 10 glycidyl units on average) | |
| Adhesive layer: | |
| Alkali-treated gelatin | 6.7 g/m² |
| Nonylphenylpolyglycidyl ether | 260 mg/m² |
| (Containing 10 glycidyl units on average) | |

A comparative multilayer analytical element for the determination of glucose was thus prepared in the same manner as Example 3 except the above.

EXAMPLE 4

The two analytical elements prepared in Example 3 and comparative Example 3 were evaluated as follows.

In order to make each calibration curve, six human plasmas having different glucose concentrations were prepared, and respective glucose concentrations were determined by the hexokinase-G-6-PDH method. Subsequently, each of the same plasmas was spotted on the spreading layer of each analytical element mounted on the slide frame, and incubated at 37° C. for 6 minutes. Immediately, the reflective optical density of the chromogen-containing layer or the color forming reagent layer was measured from the side of the support by reflection photometry using a visible light having a central wavelength at 540 nm.

The results are shown in Table 3.

TABLE 3

| Glucose Concentration | Reflective Optical Density | |
|---|---|---|
| mg/dl | Example 3 | Comparative 3 |
| 70 | 0.400 | 0.373 |
| 108 | 0.480 | 0.461 |
| 252 | 0.785 | 0.730 |
| 365 | 0.984 | 0.865 |
| 453 | 1.115 | 0.955 |
| 553 | 1.250 | 1.015 |

As shown in Table 3, since the slope of the calibration curve is large over a wide range in the analytical element of the invention, it provides accurate results.

We claim:

1. A dry multilayer analytical element for the determination of an analyte in an aqueous liquid sample by measuring the amount of hydrogen peroxide produced from the interaction of the analyte with an oxidase, comprising, in this order, a light-transmissive water-impermeable support, a chromogen-containing layer which produces an optically detectable change from the interaction of hydrogen peroxide, and a peroxidatively active substance-containing layer, said element further comprising an oxidase which reacts with the analyte to prouduce hydrogen peroxide, and a ferrocyanide, with the proviso that the ferrocyanide is in a layer separate from the chromogen-containing layer and is not interposed between the support and the chromogen-containing layer.

2. The element of claim 1 wherein the respective layers are integrally laminated on said support.

3. The element of claim 1 wherein a water absorption layer of a water swellable hydrophilic polymer is interposed between the support layer and the chromogen-containing layer.

4. The element of claim 3 wherein the swelling ratio of the hydrophilic polymer is in the range from about 150% to about 2000%.

5. The element of claim 3 wherein the water absorption layer has a thickness from about 1 μm to about 100 μm in the dry state.

6. The element of claim 3 wherein the coating amount of the water absorption layer is from about 1 g/m² to about 100 g/m².

7. The element of claim 4 wherein the water absorption layer is substantially transparent.

8. The element of claim 1 wherein the chromogen-containing layer is water-absorptive and water-permeable and the chromogen is uniformly incorporated therein.

9. The element of claim 1 wherein the chromogen-containing layer has a thickness from about 3 μm to about 50 μm in the dry state.

10. The element of claim 1 wherein the chromogen-containing layer has a coating amount from about 3 g/m² to about 50 g/m².

11. The element of claim 3 wherein the peroxidatively active substance-containing layer is a porous layer or a water-absorptive water-permeable layer.

12. The element of claim 11 wherein the porous layer is a spreading layer.

13. The element of claim 11 having a color-blocking layer between the chromogen-containing layer and the porous layer.

14. The element of claim 1 wherein the amount of oxidase is from about 100 U to about 100,000 U per square meter of element.

15. The element of claim 1 wherein the amount of peroxidatively active substance is from about 2000 U to about 60,000 U per square meter of element.

16. The element of claim 1 wherein the amount of ferrocyanide is about 0.1 mmol to about 10 mmol per square meter of element.

17. The element of claim 1 wherein the amount of chromogen is from about 0.5 mmol to about 10 mmol.

18. The element of claim 17 wherein the chromogen is a coupling chromogen and a coupler is present in the chromogen-containing in an amount from about 0.5 mmol to about 40 mmol.

* * * * *